(12) United States Patent
Hara et al.

(10) Patent No.: US 9,746,411 B2
(45) Date of Patent: Aug. 29, 2017

(54) APPARATUS AND METHOD FOR EVALUATING GAS BARRIER PROPERTIES

(71) Applicant: NATIONAL INSTITUTE OF ADVANCED INDUSTRIAL SCIENCE AND TECHNOLOGY, Tokyo (JP)

(72) Inventors: Shigeki Hara, Tsukuba (JP); Masakazu Mukaida, Tsukuba (JP); Nobuo Hara, Tsukuba (JP); Hiroyuki Suda, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 102 days.

(21) Appl. No.: 14/765,297

(22) PCT Filed: Jan. 30, 2014

(86) PCT No.: PCT/JP2014/052166
§ 371 (c)(1),
(2) Date: Jul. 31, 2015

(87) PCT Pub. No.: WO2014/119689
PCT Pub. Date: Aug. 7, 2014

(65) Prior Publication Data
US 2015/0369720 A1   Dec. 24, 2015

(30) Foreign Application Priority Data

Jan. 31, 2013 (JP) .................................. 2013-017822
Dec. 26, 2013 (JP) .................................. 2013-270502

(51) Int. Cl.
*G01N 15/08* (2006.01)

(52) U.S. Cl.
CPC ...... *G01N 15/0826* (2013.01); *G01N 15/0806* (2013.01); *G01N 2015/086* (2013.01); *G01N 2015/0846* (2013.01)

(58) Field of Classification Search
CPC .............. G01N 15/08; G01N 15/0806; G01N 15/0826; G01N 15/00; G01N 2015/0846; G01N 2015/086
See application file for complete search history.

(56) References Cited

U.S. PATENT DOCUMENTS

| 8,117,899 B2* | 2/2012 | Piombini | ........... G01N 15/0826 73/38 |
| 2004/0123646 A1* | 7/2004 | Echigo | ............... G01N 15/0826 73/38 |

(Continued)

FOREIGN PATENT DOCUMENTS

| CN | 2148326 Y | 12/1993 |
| CN | 102141504 A | 8/2011 |

(Continued)

OTHER PUBLICATIONS

Extended European Search Report, issued Sep. 7, 2016, for European Application No. 14746091.9.

(Continued)

*Primary Examiner* — Nguyen Ha
(74) *Attorney, Agent, or Firm* — Birch, Stewart, Kolasch & Birch, LLP

(57) ABSTRACT

An apparatus for evaluating gas barrier properties, containing a polymer-containing support for supporting a sample, a chamber on a permeation side, and a detection unit, in which the support is connected with an opening of the chamber on the permeation side, and in which glass transition point of the polymer contained in the support is 100° C. or higher.

6 Claims, 4 Drawing Sheets

(56) References Cited

U.S. PATENT DOCUMENTS

| | | | |
|---|---|---|---|
| 2005/0092068 A1* | 5/2005 | Ascheman | G01N 15/0826 73/38 |
| 2007/0186622 A1* | 8/2007 | Firon | G01N 15/0826 73/38 |
| 2008/0060417 A1* | 3/2008 | DeRoos | G01N 15/0826 73/38 |
| 2010/0294025 A1 | 11/2010 | Omori et al. | |
| 2014/0013825 A1 | 1/2014 | Liu et al. | |

FOREIGN PATENT DOCUMENTS

| | | | | |
|---|---|---|---|---|
| CN | 102628785 A | | 8/2012 | |
| EP | 2 952 876 A1 | | 12/2015 | |
| EP | 2 952 877 A1 | | 12/2015 | |
| JP | 59142438 A | * | 8/1984 | G01N 15/08 |
| JP | 06-241978 A | | 9/1994 | |
| JP | 2001-264237 A | | 9/2001 | |
| JP | 2007-64663 A | | 9/2001 | |
| JP | 2002-35733 A | | 12/2002 | |
| JP | 2005-017172 A | | 1/2005 | |
| JP | 2008-170358 A | | 7/2008 | |
| JP | 2010-190751 A | | 9/2010 | |
| WO | WO 2009/041632 A1 | | 4/2009 | |

OTHER PUBLICATIONS

Giannelis, "Polymer Layered Silicate Nanocomposites," Advanced Materials, vol. 8, No. 1, Jan. 1, 1996, pp. 29-35, XP-000551307.

"Plastics—Film and sheeting—Determination of water vapour transmission rate—Instrumental method.", JIS K7129-2008, Japanese Standards Association, Mar. 21, 2008 (with translation).

"Testing Method for Gas Transmission Rate through Plastic Film and Sheeting", JIS K7126-1987 (A method), Japanese Standards Association, pp. 685-688, 1999.

"Testing Method for Gas Transmission Rate through Plastic Film and Sheeting", JIS K7126-1987 (B method), Japanese Standards Association, pp. 685-688, 1999.

International Search Report issued in PCT/JP2014/052166 dated Apr. 1, 2014.

Extended European Search Report, issued Sep. 7, 2016, for European Application No. 14746763.3.

Chinese Office Action and Search Report for Chinese Application No. 201480006895.8, dated Dec. 19, 2016, with an English translation thereof.

* cited by examiner

APPARATUS AND METHOD FOR EVALUATING GAS BARRIER PROPERTIES

TECHNICAL FIELD

The present art relates to an apparatus and a method for evaluating gas barrier properties of a film.

BACKGROUND ART

In fields, such as organic electronics and food packaging, a need is recently being felt for a material having lower water vapor permeability and/or oxygen permeability than up to now, more specifically a material, such as a film or sealing material having higher gas barrier properties than in the past. A high-sensitivity technology for evaluating gas barrier properties is therefore needed for the development of new materials and the inspection of products prior to shipment.

Methods for evaluating the gas barrier properties of a sample in the form of film are generally classified into an equal-pressure method and a differential-pressure method. The equal-pressure method refers to a method according to which a gas containing a test gas is introduced onto one surface (hereinafter, referred to as feed side) of the sample, and a carrier gas, such as nitrogen, is introduced onto the other surface (hereinafter, referred to as permeation side), and concentration of the test gas that permeated through the sample and is contained in the discharged carrier gas is measured by a detection unit comprising an infrared sensor or the like (Non-Patent Literature 1, Non-Patent Literature 2). A method is known in which a quartz resonator moisture meter or a mass spectrometer is used for high-sensitivity evaluation, and a system is also known in which the space on the permeation side is temporarily closed to concentrate the test gas permeated through the sample, and the resultant concentrated gas is then introduced into a detection unit (Patent Literature 1 and Patent Literature 2).

The differential-pressure method refers to a method in which the space on the permeation side is decompressed by a vacuum pump, and then a valve is once closed to isolate the space from an external environment, a test-gas-containing gas is introduced into a feed-side space, and pressure rise on the permeation side in association with gas permeation is then measured by a detection unit formed of a pressure gauge or the like (Non-Patent Literature 3). A method is also known in which a mass spectrometer is used for evaluating water vapor barrier properties of a film having high barrier properties (Patent Literature 3, Patent Literature 4, and Patent Literature 5). In the differential-pressure method, it is necessary to support the sample against the pressure difference between the feed side and the permeation side, and a technique has been disclosed in which a porous stainless steel base material (Patent Literature 3, and Patent Literature 5), a polymer/a water-permeable glass (Patent Literature 4) or the like is used.

CITATION LIST

Patent Literatures

Patent Literature 1: International Publication No. WO2009/041632
Patent Literature 2: JP-A-2010-190751 ("JP-A" means unexamined published Japanese patent application)
Patent Literature 3: JP-A-H06 (1994)-241978
Patent Literature 4: JP-A-2002-357533
Patent Literature 5: JP-A-2005-17172

Non-patent Literature 1: JIS K7126-1987 (B method)
Non-patent Literature 2: JIS K7129-1992
Non-patent Literature 3: JIS K7126-1987 (A method)

SUMMARY OF INVENTION

Technical Problem

In the equal-pressure method, analysis of a component to be evaluated in a large amount of carrier gas is required at a ppb level. However, high-sensitivity gas analysis technologies at this level are limited. Furthermore, water vapor and oxygen are contained in the carrier gas as impurities before the carrier gas is introduced into an evaluation apparatus, which limits evaluation sensitivity.

The differential-pressure method requires a support, but a sample to be evaluated deforms along recesses and projections (protrusions) on a surface of the support, with the result that a concern arises regarding the gas barrier properties being adversely affected.

In both methods, atmospheric air is entrained into the apparatus upon mounting the sample in the apparatus and a long period of time ranging from several days to several weeks is required to eliminate the influence (particularly of the water vapor), which poses a major obstacle to material development or inspection of products prior to shipment.

The present invention is contemplated for providing an apparatus and a method for evaluating gas barrier properties according to which samples can be exchanged while maintaining a favorable environment inside a permeation-side chamber.

Solution to Problem

The present invention is contemplated for providing an apparatus for evaluating gas barrier properties, comprising a polymer-containing support for supporting a sample, a chamber on a permeation side, and a detection unit, in which the support is connected with an opening of the chamber on the permeation side, and in which glass transition point of the polymer contained in the support is 100° C. or higher.

The present invention is also contemplated for providing a method for evaluating gas barrier properties, comprising providing a polymer-containing support for supporting a sample, a chamber on a permeation side, and a detection unit, the support being connected with an opening of the chamber on the permeation side, and glass transition point of the polymer contained in the support being 100° C. or higher, wherein the chamber on the permeation side is heated to 100° C. or higher before mounting the sample.

Advantageous Effects of Invention

According to the present invention, samples can be exchanged while maintaining a favorable environment inside a permeation-side chamber. As a result, the following various advantageous effects are obtained:
(1) gas barrier properties can be evaluated immediately after the sample is mounted;
(2) the operation and structure of the apparatus are simple; and
(3) a detection unit with high sensitivity can be readily used.

Furthermore, a dense, even, and smooth support can be used, and therefore the following advantageous effects are obtained:

(4) no risk of sample deformation adversely affecting gas barrier performance;
(5) gas barrier properties of a sample of a structure close to the organic electronic structure to be actually used can be evaluated; and
(6) evaluation time can be shortened and evaluation sensitivity can be improved by changing pressures on the feed side and the permeation side.

Further, by utilizing a method using a pressure gauge or a mass spectrometer, use of carrier gas becomes unnecessary and the disadvantages of the equal-pressure method and the differential-pressure method can be simultaneously overcome.

Other and further features and advantages of the invention will appear more fully from the following description, appropriately referring to the accompanying drawing.

MODE FOR CARRYING OUT THE INVENTION

Figure 1:
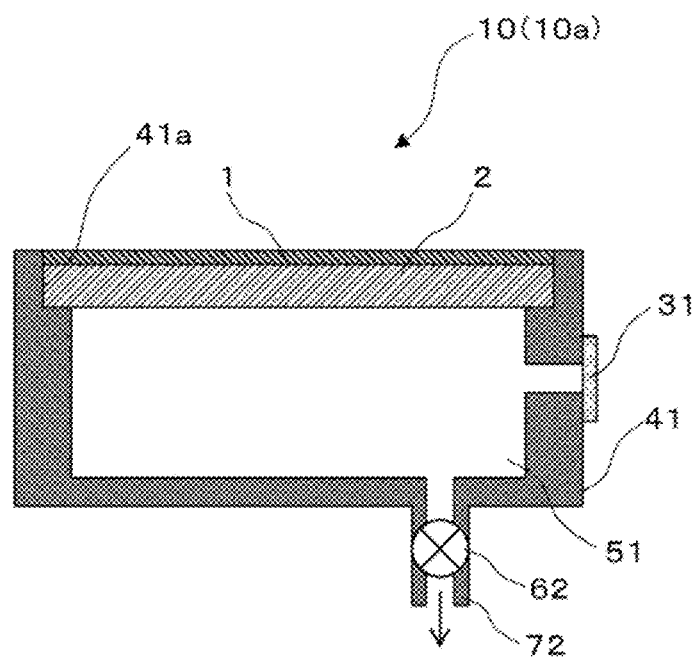
FIG. 1 is a cross-sectional view schematically showing a first embodiment as one preferred embodiment of an apparatus for evaluating gas barrier properties of the present invention.

Various methods have been reported for evaluating gas barrier properties with high sensitivity, but almost no study has been conducted on a support to be used therein. More specifically, no noteworthy innovations have been reported regarding support performance and method of use. The support material has so far been selected only from a viewpoint of excellent gas permeability causing no hindrance to evaluation of the gas barrier properties while the support supports the sample.

In order to eliminate the influence of atmospheric air entrained into the apparatus, the inventors focused attention on a heating operation of the apparatus called baking that is generally performed in a vacuum apparatus, and diligently continued to conduct study on a method of application to the apparatus for evaluating the barrier properties. As a result, the inventors realized that by providing the support with heat resistance and also connecting it with the opening of the permeation-side chamber to form a structure that is not detached in exchange of samples, baking becomes possible and the effect thereof can be maintained even after samples are exchanged. In the course of completing this invention, the inventors additionally found that other various advantageous effects are obtained, and have completed the present invention.

The apparatus for evaluating gas barrier properties of the present invention, comprises a polymer-containing support for supporting a sample, a chamber on a permeation side, and a detection unit, in which the support is connected with an opening of the chamber on the permeation side, and in which glass transition point of the polymer contained in the support is 100° C. or higher.

The above-described support is connected with the opening of the permeation-side chamber so as to close the opening. The term "connection" herein means that the support and the permeation-side chamber are united even when samples are exchanged and that gas flowing into the permeation-side chamber through a boundary between the support and the permeation-side chamber is less than gas permeating through the support and flowing into the permeation-side chamber. For this purpose, the support and the permeation-side chamber need only to be fixed by using an adhesive. Alternatively, the support may be attached to the permeation-side chamber using a gasket. In addition, a structure may be optionally formed in which the support can be detached from the permeation-side chamber for repairing the apparatus, or the like. For example, the support can be connected with the permeation-side chamber, using bolts separate from those for mounting the sample. Thus, the support is not detached for every exchange of the samples, and can be readily replaced when, for example, repairing the apparatus.

Gas-transmission rate (gas permeance) P [mol/m$^2$sPa] of a material (generally a sheet, a film, or a tube) that divides a space in two is an indicator defined by formula (A).

$$J=P(p_1-p_2) \tag{A}$$

wherein $p_1$ [Pa] and $p_2$ [Pa] each represent a partial pressure of a gas under observation (test gas) on both sides across the material, and J [mol/m$^2$s] represents permeation flux of this gas permeating from a side surface in contact with $p_1$ to a side surface in contact with $p_2$.

A transmission rate (water vapor-transmission rate) of the support with respect to water vapor suitable in the present invention is $1\times10^{-8}$ mol/m$^2$sPa to $1\times10^{-14}$ mol/m$^2$ sPa, preferably $5\times10^{-9}$ mol/m$^2$sPa to $1\times10^{-13}$ mol/m$^2$sPa, and further preferably $1\times10^{-9}$ mol/m$^2$sPa to $1\times10^{-12}$ mol/m$^2$sPa. A value of $1\times10^{-19}$ mol/m$^2$sPa corresponds to 1 g/m$^2$ day in terms of WVTR (indicator showing water vapor-transmission rate broadly used regarding water vapor barrier properties) from 40° C., 90% RH (water vapor pressure 6.6 kPa) to vacuum (0 kPa). Moreover, a porous support generally has a water vapor-transmission rate larger than $1\times10^{-7}$ mol/m$^2$sPa. When a support having a water vapor-transmission rate larger than $1\times10^{-8}$ mol/m$^2$sPa is used, flow of an atmospheric air component into the permeation-side chamber in exchange of the samples increases, and an advantage of the present invention is partially adversely affected. On the other hand, when a support having a water vapor-transmission rate smaller than $1\times10^{-14}$ mol/m$^2$sPa is used, evaluation of a sample at a level of $1\times10^{-14}$ mol/m$^2$sPa ($10^{-4}$ g/m$^2$ day) in water vapor-transmission rate becomes difficult.

Also in an evaluation of a gas other than water vapor, a support material should be selected on the basis of the water vapor-transmission rate as mentioned above. This is because suppression of water vapor flowing into the permeation-side chamber in exchange of the samples exhibits advantageous effects of the present invention, such as achievement of high sensitivity and speed increase, also in the evaluation on the gas other than the water vapor. In addition, a support having a transmittance rate matched to the gas may be appropriately selected. In addition, a support having a high water vapor-transmission rate generally exhibits a high transmission rate also for oxygen, nitrogen, carbon dioxide, or the like. It therefore often suffices to select the support material on the basis of the water vapor-transmission rate.

As mentioned above, it is unnecessary to use a porous body for the support in order to realize this water vapor-transmission rate. Rather, it is better to use a dense raw material. The term "dense" herein means absence of micropores that have a pore diameter exceeding 1 nm and penetrate from one surface of the support in contact with the sample to the other surface thereof. For this, it suffices if no micropores having a pore size of 1 nm are found when a surface of the support is observed by a surface observation means, such as a scanning electron microscope or an atomic force microscope. Non-penetrating micropores (for example, surface dents) and penetrating micropores are undistinguishable by these surface observation means. However, insofar as absence of micropores on the surface can be confirmed, absence of penetrating micropores is actually confirmed. In addition, there are some instances in which interstices at an atomic level of a polymer chain are referred to as "micropores" in the polymer material. However, the interstices at the atomic level (namely, nm or less) formed between the polymer chains are not considered to be the micropores herein.

In the present invention, the permeation-side chamber and a pipe communicating therewith are heated to 100° C. or higher (called baking) to enable sufficient elimination of water vapor adhered on an inner wall. Then, the chamber and the pipe are cooled to a temperature at which work can be performed, whereafter the sample is mounted. Glass transition point of the polymer contained in the support is 100° C. or higher, and therefore the support can withstand baking for eliminating the water vapor. Moreover, the support is connected with the permeation-side chamber, to allow mounting of the sample in the structure as it is. A favorable environment (degree of vacuum, gas concentration, and the like) on the permeation side after baking can be maintained by adopting such a structure, and it therefore becomes unnecessary to dry up the water vapor on the inner wall of the permeation-side chamber after the sample is mounted. The gas barrier properties can therefore be immediately evaluated.

In a conventional apparatus, it is necessary to once open the space on the permeation side to atmospheric air when exchanging samples. As a result, water vapor in atmospheric air enters the permeation-side chamber, and adheres onto the inner wall of the permeation-side chamber. After the sample is mounted, the inside of the permeation-side chamber is exhausted or a carrier gas is introduced thereinto. However, several days have been necessary for the water vapor adsorbed on the inner wall of the permeation-side chamber to dry up after exchanging samples. Heating is sometimes performed to reduce the time period for elimination of the water vapor, but many samples are not sufficiently heat resistance, and about 80° C. is the limit.

However, a baking temperature of 80° C. is inadequate. At least 100° C., the boiling point of water, or higher is preferred. In the vacuum apparatus, in order to eliminate water vapor adhered on the inner wall of the permeation-side chamber in general, baking is performed generally at 150° C. (in the case of a chamber made of aluminum), and further preferably at 200° C. or higher (in particular, in the case of a chamber made of stainless steel). Therefore, the glass transition point of the polymer contained in the support suitable in the present invention is also 100° C. or higher, further preferably 150° C. or higher, and still further preferably 200° C. or higher. Thus, an effect that is not obtainable by the conventional apparatus for evaluating barrier properties can be obtained.

Further, it is unnecessary to open the space on the permeation side to atmospheric air when exchanging samples, and an operation of opening and closing various kinds of valves and starting and stopping a vacuum pump on the permeation side therefore becomes unnecessary to some extent. As a result, the operation and structure of the apparatus become simple and inexpensive. The risk of accidentally damaging a detection unit also becomes low, and therefore a detection unit with high sensitivity (pressure gauge or the like) can be attached on the permeation side without providing a particular protection mechanism, and can even be operated continuously in some cases.

The support may be a dense material as described above, and therefore an apparatus for evaluating gas barrier properties can be formed in which a surface adjacent to the sample is smooth. Accordingly, it is unnecessary to worry about deformation being caused by a pressure difference between the feed side and the permeation side of the test gas. Samples in the form of film often have a layer structure. In the apparatus in which a porous support is used, there has been a risk of deformation of the sample along the shape of the micropores, damaging the layer structure, and adversely affecting the gas barrier properties. Moreover, when the porous support is used, structural discontinuity, such as a level difference, is often caused at a boundary between a dense peripheral portion required for sealing and a porous region. The support for use in the present invention is dense over its entire area, and sealing and sample support can therefore be made by using a smooth sheet without any boundary at all. In addition, from the above-described viewpoints, within the range in which no inconvenience arises, fine recesses and projections, moderate recesses and projections (undulation), or some scratches can obviously be tolerated. The term "smooth" in the present invention means absence of level differences, recesses and projections exceeding 10 μm elevation difference within a distance of 100 μm. The term preferably means absence of level differences, recesses and projections exceeding 1 μm elevation difference within a distance of 100 μm, and further preferably absence of level differences, recesses and projections exceeding 0.1 μm elevation difference within a distance of 100 μm. The reason for this is that the thickness of the sample to be evaluated is generally several tens of μm, and the difference of elevation is required to be at least smaller than the thickness. If the difference of elevation is 1/100 or less of the thickness of the sample, no defect is occurred in the sample.

Further, an apparatus for evaluating gas barrier properties can be formed in which the above-described support is in the form of sheet. The support should have an optimum shape matched to the shape of the sample in order to support the sample to be evaluated. The sample is often a flat film, and in this case, a support in the form of sheet is suitable. The pressure applied to the sample in the form of film at this time is atmospheric pressure, and the other side is formed in a smooth and dense wall (support), which is close to a structure actually used in organic electronics. According to the equal-pressure method, one of the two conventional methods, the sample is brought in contact with a gas phase on both sides. According to the differential-pressure method, the sample is normally evaluated in a state of being pressed onto an uneven porous support, which is clearly different from the environment under which the apparatus is used in organic electronics.

Further, an apparatus for evaluating gas barrier properties can be formed in which the thickness of the above-described support is generally 1 mm to 20 mm, preferably 2 mm to 15 mm, and further preferably 5 mm to 10 mm. This thickness ensures the strength of the support, to facilitate handling of the apparatus. If the support is too thin, the support is damaged or bent by the pressure difference between the feed side and the permeation side, which is unpreferable. If the support is too thick, gas permeation from a cross-section around the support cannot be ignored, and overcoming this problem makes the apparatus complicated. In addition, the term "thickness" herein means an apparent total thickness. For example, when two sheets of a porous metal sheet and a polymer sheet are stacked and used, the thickness is the total thickness of those.

The polymer contained in the above-described support means, for example, one having a mass average molecular weight of 10,000 or more. For example, the polymer can be selected from among polycarbonate (145 to 150° C.), polyimide (285 to 420° C.), polyether ether ketone (143° C.), polyether sulfone (225° C.), and polyamide-imide (280 to 290° C.) (parenthetical numerals indicate glass transition point). On the contrary, many general-purpose polymer materials having a low glass transition temperature (glass transition point) are unsuitable, such as polyethylene (−120° C.), polyvinyl chloride (70 to 87° C.), polystyrene (80 to 100° C.), acryl (70° C.), Nylon 66 (50° C.), and polyethylene terephthalate (69° C.). In addition, the glass transition point significantly depends on molecular weight, composition, and production process, and therefore it is necessary to suitably select the polymer based on the characteristics of each product, irrespective of the above described polymer classification.

Further, the above-described support of the apparatus for evaluating gas barrier properties is preferably an organic/inorganic composite. By this, the gas permeability can be held low. Specifically, a support having silica, diamond-like carbon, or the like coated on a polymer surface is suitable. A composite material in which an inorganic raw material, such as clay mineral and silica, having low gas permeability is mixed into a polymer material is also suitable.

Further, the apparatus for evaluating gas barrier properties is preferably constituted so that pressure inside the permeation-side chamber is lower than atmospheric pressure. By atmospheric pressure is meant standard atmospheric pressure of 101.325 kPa. Further, the apparatus for evaluating gas barrier properties can also be formed so that the pressure inside the feed-side chamber is higher than standard atmospheric pressure. As the present invention uses the support, it is unnecessary to apply the same pressure to the permeation side and the feed side. Partial pressure difference of the test gases on opposite sides of the sample can also be increased by reducing the pressure on the permeation side or raising the pressure on the feed side. As shown in formula (A), the gas permeation flux is generally proportional to the partial pressure difference, and therefore if the partial pressure difference is doubled, the permeation flux is also doubled. Accordingly, evaluation time period can be cut in half. Alternatively, if the same time period is taken, sensitivity can be doubled. Moreover, the evaluation time period can be further shortened or the sensitivity can also be further improved by increasing the partial pressure difference. Thus, the pressure can be freely changed, and therefore the gas permeability relative to various partial pressure differences can be readily evaluated, and apparatus performance can be verified from many evaluation data obtained. On the other hand, it is necessary to apply equal pressure on both sides of the sample in an ordinary equal-pressure-type apparatus for evaluating gas barrier properties, and complicated control is required for equalizing the pressure on both sides of the sample at a pressure other than atmospheric pressure.

Further, the aforesaid detection unit of the apparatus for evaluating gas barrier properties is preferably a pressure gauge. According to the present invention, gas permeability can be evaluated by using a pressure gauge. In particular, the sensitivity of a pressure gauge (namely, a vacuum gauge) in a low-pressure range is significantly high, some being capable of measuring down to $10^{-12}$ Pa. Pressure sensitivity required for evaluating water vapor barrier properties at a level of $10^{-6}$ g/m$^2$ day is about $10^{-1}$ Pa, so that there is a margin of measurement sensitivity. Accordingly, the barrier properties can be readily evaluated to a high sensitivity of $10^{-6}$ g/m$^2$ day. On the other hand, the prior art method and apparatus for evaluation gas barrier properties having a sensitivity of $10^{-6}$ g/m$^2$ day are limited.

When a pressure gauge is used, the gas permeability, namely the gas barrier properties of the sample can be evaluated as described below.

Volume of the permeation-side chamber is expressed as V [m$^3$], and gas permeation region of the sample is expressed as S [m$^2$]. Partial pressure of the test gas on the feed side is expressed as $p^f$ [Pa], and partial pressure on the permeation side is expressed as $p^p$ [Pa]. If the chamber is isolated from the external environment by closing the valve communicating with the permeation-side chamber, the total number n [mol] of molecules inside the permeation-side chamber increases by Δn [mol] in Δt [s], due to the gas permeating through the sample. As a result, an increase of Δ$p^p$ [Pa] appears inside the permeation-side chamber. At this time, if temperature inside the permeation-side chamber is expressed as T [K], and gas constant is expressed as R (=8.314 J/molK), formula (1) holds.

$$\Delta n = \frac{V}{RT}\Delta p^p \tag{1}$$

Permeation flux J [mol/m$^2$s] of the test gas is given by formula (2).

$$J = \frac{1}{S}\frac{\Delta n}{\Delta t} = \frac{V}{RTS}\frac{\Delta p^p}{\Delta t} \tag{2}$$

Gas-transmission rate P$^{tot}$ [mol/m$^2$sPa] of the sample and support combined can be defined by formula (3).

$$J = P^{tot}(p^f - p^p) \tag{3}$$

Formula (4) is obtained by substituting formula (2) into formula (3).

$$P^{tot} = \frac{1}{S(p^f - p^p)}\frac{\Delta n}{\Delta t} = \frac{V}{RTS(p^f - p^p)}\frac{\Delta p^p}{\Delta t} \tag{4}$$

Gas-transmission rates P$^f$ and P$^s$ of the sample and the support can be expressed, respectively, by formulas (5) and (6) by using the partial pressure p$^b$ [Pa] of the test gas on their interface.

$$J^f = P^f(p^f - p^b) \tag{5}$$

$$J^s = P^s(p^b - p^p) \tag{6}$$

In a stable state, the permeation fluxes are equal. More specifically, formula (7) holds.

$$J^f = J^s = J \tag{7}$$

Formula (8) is obtained from formulas (5), (6), and (7).

$$J = \frac{P^f P^s}{P^f + P^s}(p^f - p^p) \tag{8}$$

For comparison with formula (3), formula (9) is obtained as the relationship between the gas-transmission rates of the support and the whole.

$$P^{tot} = \frac{P^f P^s}{P^f + P^s} \tag{9}$$

If the gas-transmission rate $P^s$ of the support is determined in advance, the gas-transmission rate $P^f$ of the sample can be obtained from formula (10) using $P^{tot}$ obtained by applying formula (4) to test results.

$$P^f = \frac{P^{tot} P^s}{P^s - P^{tot}} \tag{10}$$

Further, when the gas-transmission rate of the sample is low and $P^s \gg P^f$, for example, when the rates differ by two or more orders of ten, formula (9) can be approximated by formula (11).

$$P^f = P^{tot} \tag{11}$$

More specifically, the gas-transmission rate of the sample is given by formula (12).

$$P^f = \frac{V}{RTS(p^f - p^p)} \frac{\Delta p^p}{\Delta t} \tag{12}$$

When the test gas is water vapor (molecular weight: 18 g/mol), the rate can be expressed as shown below using WVTR [g/m² day] as the unit.

$$WVTR = 18 \times 24 \times 60 \times 60 \times J = \frac{1.56 \times 10^6 \times V}{RTS} \frac{\Delta p^p}{\Delta t} \tag{13}$$

Conversely, when the gas-transmission rate $P^s$ of the support is lower than the gas-transmission rate $P^f$ of the sample and $P^s \ll P^f$, evaluation of the gas-transmission rate $P^f$ of the sample becomes significantly difficult. More specifically, it is important to note that the gas-transmission rate $P^s$ of the support should be higher than, or at least equal to, the gas-transmission rate $P^f$ of the sample.

Further, the aforesaid detection unit of the apparatus for evaluating gas barrier properties is preferably a mass spectrometer.

A partial pressure of the gas inside the permeation-side chamber can be directly evaluated using the mass spectrometer. When humidified nitrogen is used as feed gas, not only water vapor but also nitrogen permeates through to some extent. The partial pressure of water vapor can be evaluated by using the mass spectrometer, and therefore an exact evaluation can be made. In addition, the water vapor-transmission rate is generally larger than that of other gases, and therefore when the pressure gauge is used instead of the mass spectrometer, the rate can be approximated by regarding the total pressure inside the permeation-side chamber as a water vapor partial pressure.

Thus, according to the present invention in which the gas barrier properties of the sample are evaluated from a pressure increase inside the permeation-side chamber, a high-purity carrier gas is unnecessary, and thus a disadvantage of the equal-pressure method can be overcome. Furthermore, an even support can be used, and therefore a disadvantage of sample deformation that is a concern in the ordinary differential-pressure method can also be eliminated. Moreover, no atmospheric air is entrained into the permeation-side chamber upon mounting the sample, and the gas barrier properties can be immediately evaluated.

Further, the present invention can be utilized also in a method that passes carrier gas into the permeation-side chamber, and the gas barrier properties can be immediately evaluated without entraining atmospheric air into the permeation-side chamber upon mounting the sample. The advantageous effects described above, such as that the operation and the structure of the apparatus are simple, and that a detection unit with high sensitivity can be readily used, are simultaneously obtained.

When the carrier gas is passed, the gas barrier properties can be evaluated as described below. For example, high purity nitrogen is introduced into the permeation-side chamber, and flow rate Q [mol/s] of the carrier gas discharged from the permeation-side chamber and concentration C [ppm] of permeated test gas are measured. If the total pressure inside the permeation-side chamber is $P_0$, partial pressure $p^p$ [Pa] of the test gas on the permeation side is given by formula (14).

$$p^p = 10^{-6} C P_0 \tag{14}$$

On the other hand, permeation flux J [mol/m²s] of the test gas is given by formula (15) using gas permeation region S [m²] of the sample.

$$J = \frac{10^{-6} CQ}{S} \tag{15}$$

$P^{tot}$ is determined by formula (3) by using $p^p$ and J obtained by formulas (14) and (15), and substituting the resulting value into formula (10) to obtain gas-transmission rate $P^f$ of the sample. Further, when the gas-transmission rate of the sample is low and $P^s \gg P^f$, the rate can be approximated by a formula: $P^f = P^{tot}$, and therefore the transmission rate of the sample is therefore calculated by formula (16).

$$P^f = \frac{10^{-6} CQ}{S(p^f - 10^{-6} C P_0)} \tag{16}$$

When the test gas is water vapor, the rate can be expressed as shown below using WVTR [g/m² day] as the unit.

$$WVTR = 18 \times 24 \times 60 \times 60 \times J = \frac{1.56 CQ}{S} \tag{17}$$

As shown in FIG. 1, an apparatus 10 (10a) for evaluating gas barrier properties according to the first embodiment is an apparatus for evaluating barrier properties against air that is installed in atmospheric air. A dense and smooth support 2 in the form of a flat sheet made of polycarbonate is fixed on an opening 41a side of a permeation-side chamber 41 using an adhesive. Excluding in evaluating the gas barrier properties, a permeation-side space 51 inside the permeation-side chamber 41 is decompressed to an industrial-level vacuum of, for example, 0.0 Pa through a valve 62 and a permeation-side gas outlet pipe 72 using a vacuum pump (not shown). Pressure inside the permeation-side chamber 41 is measured by a detection unit (pressure gauge) 31. Water vapor-transmission rate of the support 2 is $7.3 \times 10^{-11}$ mol/m²sPa, and air-transmission rate is $5 \times 10^{-13}$ mol/m²sPa.

After the apparatus 10a for evaluating gas barrier properties is started up, the permeation-side space is progressively exhausted by the vacuum pump with the permeation-side chamber 41 and the pipe communicating therewith heated to 100° C., and this condition is held for one week (baking). The glass transition point of the support polycarbonate is about 150° C., so that the permeability and shape of the support are maintained even when baked. The temperature is then lowered to room temperature and a high vacuum is maintained. Thus, in comparison with the case where no baking is applied, emission of oxygen and water vapor from the inner wall of the permeation-side chamber can be reduced, to enable measurement with high sensitivity.

When gas barrier properties are evaluated, a sample 1 in the form of film is arranged in contact with the support 2, and the periphery of the sample 1 is sealed with a sealing material, for example, one made of beeswax. Then, if the valve 62 is closed, pressure in the permeation-side space 51 inside the permeation-side chamber 41 rises, due to air flowing through the sample 1 and the support 2 into the permeation-side space 51 inside the permeation-side chamber 41. Change thereof over time is examined. Assuming the area of the gas permeation region of the sample 1 to be $1 \times 10^{-3}$ m², the volume of the permeation-side chamber 41 to be $1 \times 10^{-5}$ m³, and the pressure to increase by 250 Pa in one day (86,400 seconds) at 25° C., the air-transmission rate of the sample 1 and support 2 combined calculated by formula (4) is $1.15 \times 10^{-13}$ mol/m²sPa. In addition, the rate is calculated under the conditions of: $p^f$=101.325 Pa and $p^p$=0 Pa. Using this value and the air-transmission rate of the support 2, the air-transmission rate of the sample 1 can be calculated by formula (10) to be $1.50 \times 10^{-13}$ mol/m²sPa.

If the pressure increases only by 25 Pa in one day (86,400 seconds) in the measurement of a different sample under identical conditions, the air-transmission rate of the sample 1 and support 2 in combination calculated by formula (4) is $1.15 \times 10^{-14}$ mol/m²sPa. Using this value and the air-transmission rate of the support 2, the air-transmission rate of the sample 1 calculated by formula (10) is $1.18 \times 10^{-14}$ mol/m²sPa. This value differs by only 2% from the air-transmission rate of the sample 1 and support 2 in combination. More specifically, with regard to a sample having low air-transmission rate, the air-transmission rate of the sample 1 and support 2 in combination is itself deemed in accordance with formula (11) to be the air-transmission rate of the sample 1.

After the measurement, the valve 62 is opened and the permeation-side space 51 inside the permeation-side chamber 41 is exhausted. With this state maintained as it is, the beeswax is melted by raising the temperature several tens of ° C., whereafter the sample 1 can be demounted.

By so configuring the apparatus 10 (10a) for evaluating gas barrier properties, the gas barrier properties can be immediately measured after the sample 1 is mounted. Further, gas (air)-transmission rate of the sample 1 can be evaluated with its shape maintained by the support 2. The support 2 is dense and smooth, so that the sample 1 sustains no deformation, resulting in no damage. Furthermore, the gas-transmission rate can be evaluated with high sensitivity by using an inexpensive pressure gauge without using a complicated and expensive analytical apparatus.

Figure 2:
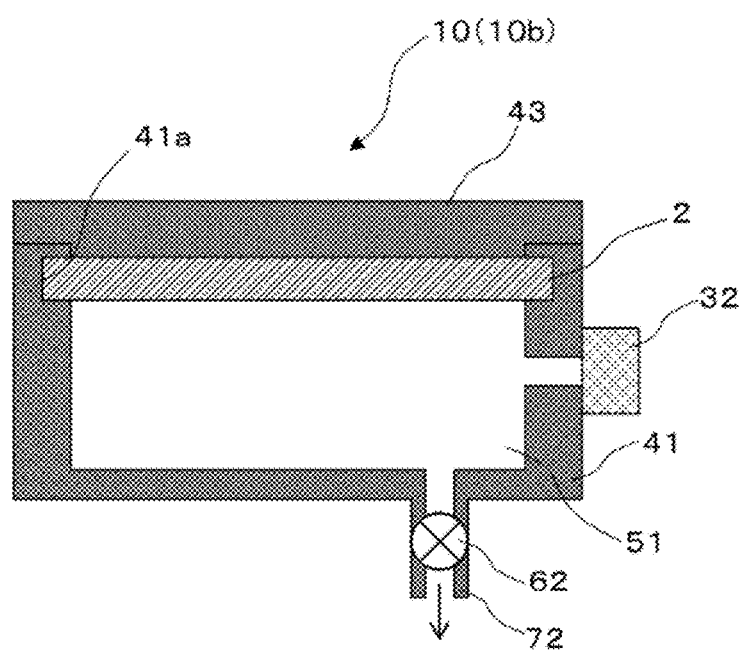
FIG. 2 is a cross-sectional view schematically showing a second embodiment of an apparatus for evaluating gas barrier properties of the present invention, and a diagram showing a state before mounting of a sample.

As shown in FIG. 2, an apparatus 10 (10b) for evaluating gas barrier properties according to the second embodiment is an apparatus for evaluating barrier properties against water vapor. The drawing shows a state before mounting a sample. A dense and smooth support 2 in the form of a flat sheet is fixed on an opening 41a side of a permeation-side chamber 41 using an adhesive. When gas barrier properties are not being evaluated, a cover 43 is placed on the support 2, and the periphery of the cover 43 is sealed with a heat-resistant gasket. A permeation-side space 51 inside the permeation-side chamber 41 is decompressed to, for example, $1 \times 10^{-4}$ Pa, using a vacuum pump (not shown) through a valve 62 and a permeation-side gas outlet pipe 72. Water vapor partial pressure in the permeation-side space 51 inside the permeation-side chamber 41 is measured using a detection unit (mass spectrometer) 32.

For the support 2, polyimide coated with silica is used. Water vapor-transmission rate of this support is $2 \times 10^{-9}$ mol/m²sPa.

While the permeation-side space is being exhausted by the vacuum pump in this condition, the permeation-side chamber 41 and the pipe communicating therewith are heated to 200° C., and this condition is held for one week (baking). The glass transition point of polyimide is about 280° C., so that the permeability and shape of the support are maintained even when baked. Thus, in comparison with the case where no baking is applied, emission of oxygen or water vapor from the inner wall of the permeation-side chamber can be reduced, to enable measurement with high sensitivity.

Figure 3:
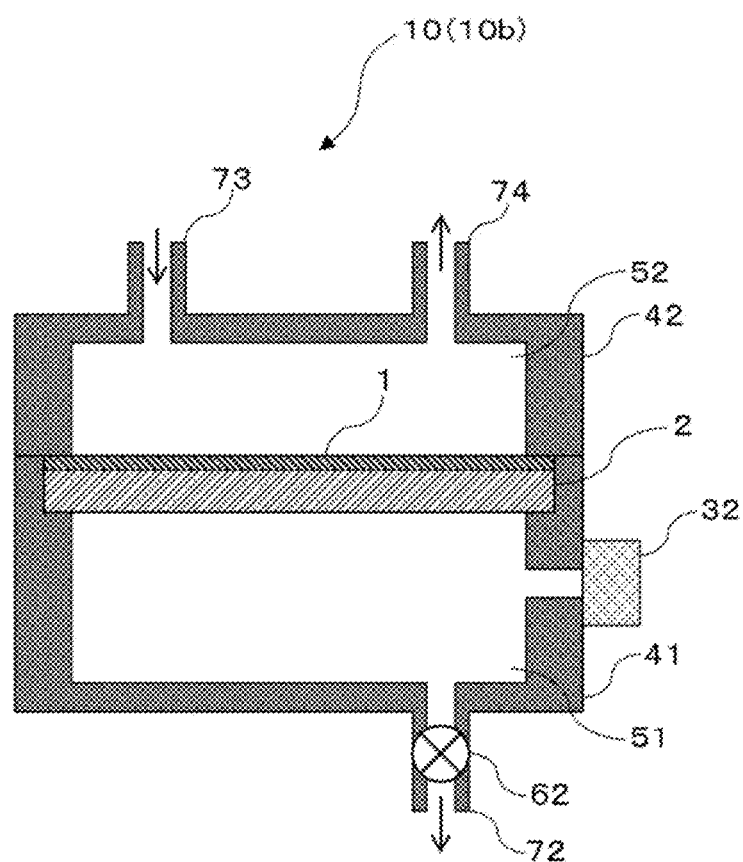
FIG. 3 is a cross-sectional view schematically showing the second embodiment of the apparatus for evaluating gas barrier properties of the present invention, and a diagram showing a state under evaluation of gas barrier properties.

As shown in FIG. 3, when gas barrier properties are to be evaluated, the cover 43 (see FIG. 2 discussed above) is detached, the sample 1 in the form of film is arranged in contact with the support 2, the periphery of the support 2 is sealed with a sealing material, for example, one made of beeswax. Further, a feed-side chamber 42 communicating with a feed-side gas inlet pipe 73 and a feed-side gas outlet pipe 74, is placed over the sample 1, and nitrogen of atmospheric pressure (standard atmospheric pressure=101.325 kPa), temperature of 40° C., and humidity of 90% RH is introduced into a feed-side space 52 inside the feed-side chamber 42 through the feed-side gas inlet pipe 73. Water vapor pressure of this feed gas amounts to 6.6 kPa. Then, if the valve 62 is closed, water vapor partial pressure in the permeation-side space 51 inside the permeation-side chamber 41 rises, due to water vapor that flows into the permeation-side space 51 inside the permeation-side chamber 41 through the sample 1 and the support 2. Change thereof over time is examined. Assuming the area of the gas permeation region of the sample 1 to be $1 \times 10^{-3}$ m², the volume of the permeation-side space 51 inside the permeation-side chamber 41 to be $5 \times 10^{-3}$ m³, and the water vapor partial pressure to increase by $1 \times 10^{-3}$ Pa in one day (86,400 seconds) at 40° C., the water vapor-transmission rate of the sample 1 and support 2 combined calculated by formula (4) is $3.4 \times 10^{-15}$ mol/m²sPa. As the water vapor-transmission rate of the support 2 is $2 \times 10^{-9}$ mol/m²sPa, the water vapor-transmission rate of the sample 1 can be calculated by formula (10) to be $3.4 \times 10^{-15}$ mol/m²sPa. The rate expressed in terms of WVTR using formula (13) is $3.5 \times 10^{-5}$ g/m² day.

By so configuring the apparatus 10b for evaluating gas barrier properties, the gas barrier properties can be immediately evaluated after the sample 1 is mounted. More specifically, the permeation-side space 51 inside the permeation-side chamber 41 is not exposed to atmospheric air upon exchanging the samples 1, so that no water vapor in atmospheric air adheres to the inner wall of the permeation-side chamber 41. As a result, decompression of the permeation-side space 51 inside the permeation-side chamber 41 in evaluation causes only limited emission of water vapor from the inner wall, so that the baseline of the water vapor partial pressure can be held to a low level. Accordingly, small change in water vapor partial pressure can be measured. In other words, the water vapor barrier properties can be evaluated with high sensitivity. The time period required for the baseline of water vapor partial pressure to lower (several days to several weeks by the conventional technology) also becomes short, so that gas barrier properties can be evaluated in a short time period.

This embodiment uses the support 2 having a water vapor-transmission rate of $1 \times 10^{-12}$ mol/m²sPa. If the operation from detaching the cover 43 to mounting the sample 1 is completed within one minute, pressure increase in the permeation-side space 51 inside the permeation-side chamber 41 due to permeation of water vapor from atmospheric air (assuming temperature of 25° C. and humidity of 50% RH, which corresponds to a water vapor pressure of 1.6 kPa), calculated using formula (4), is $5 \times 10^{-5}$ Pa, which is sufficiently small. Even when the water vapor-transmission rate of the support 2 is $1 \times 10^{-10}$ mol/m²sPa, pressure increase in mounting the sample in one minute is $5 \times 10^{-3}$ Pa. Accordingly, a sample 2 can be mounted without stopping the mass spectrometer or performing a valve operation. On the other hand, when acryl having a water vapor-transmission rate of $1.3 \times 10^{-9}$ mol/m²sPa is used for the support 2, pressure increase reaches $6 \times 10^{-2}$ Pa. Therefore, the apparatus must be stopped in the case of a mass spectrometer that does not operate at $10^{-2}$ Pa or more.

It is also a significant advantage that a detection unit 32 with high sensitivity can be safely used. The detection unit 32 with high sensitivity is designed so as to evaluate trace components, so that the unit 32 is at risk of being damaged if accidentally exposed to a normal pressure in the operation. However, according to the present invention, the permeation-side space 51 inside the permeation-side chamber 41 is held at a low pressure at all times, including the time in sample exchange, as described above, and therefore the unit 32 is free from any worry about being damaged.

The permeation-side space 51 inside the permeation-side chamber 41 is not directly exposed to atmospheric air upon exchanging samples, and the present invention therefore also has the advantage of experiencing no problem even when samples are exchanged in a place where no humidity control is conducted.

In addition, the present invention also has the advantage of the differential-pressure method, in which carrier gas of high purity is unnecessary.

In addition, nitrogen, in addition to the water vapor, is also permeated therethrough in this evaluation, and the pressure in the permeation-side space 51 inside the permeation-side chamber 41 rises. However, if, as a gas to be introduced, substantially 100% of water vapor is used in place of nitrogen, only the water vapor is permeated therethrough, and therefore as the detection unit 32, an ordinary pressure gauge can be applied in place of the mass spectrometer.

Moreover, a nitrogen-transmission rate can also be evaluated by introducing dry nitrogen thereinto. However, on the above occasion, the ordinary pressure gauge can be applied in place of the mass spectrometer.

Figure 4:
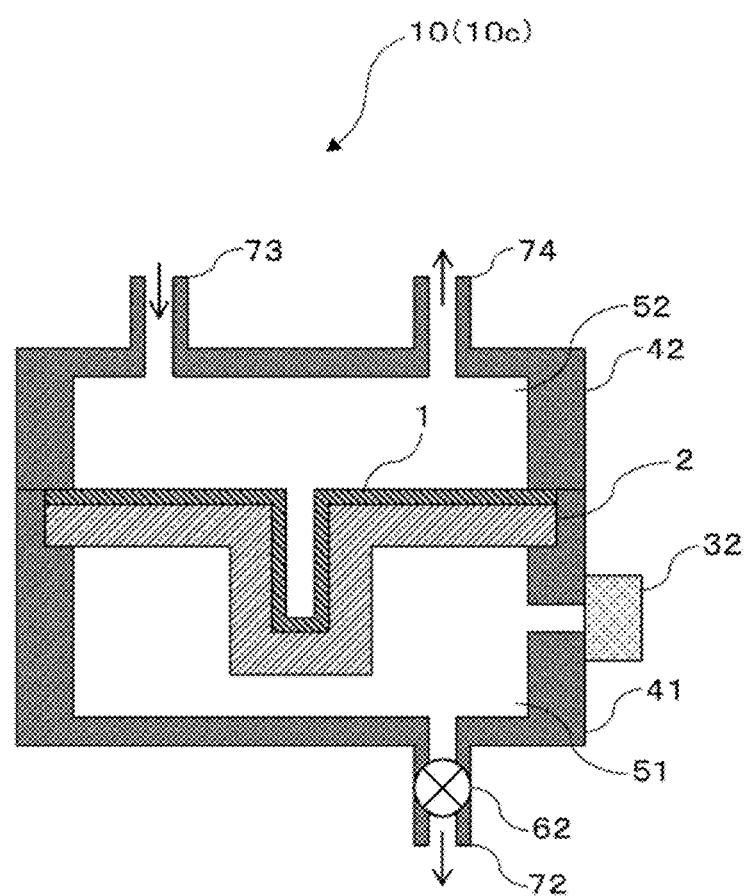
FIG. 4 is a cross-sectional view schematically showing a third embodiment of an apparatus for evaluating gas barrier properties of the present invention.

As shown in FIG. 4, an apparatus 10 (10c) for evaluating gas barrier properties according to the third embodiment has a structure similar to that of the apparatus 10b for evaluating gas barrier properties shown in FIG. 3, except that its support 2 has a shape for accommodating a sample 1 having a center projection. Thus, the present invention can be applied to samples having various shapes.

Figure 5:
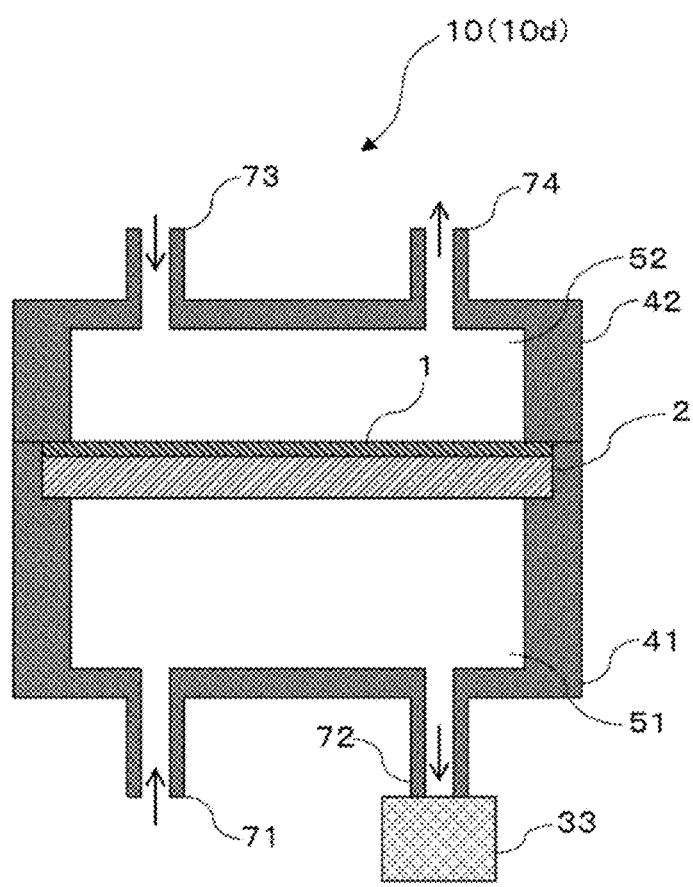
FIG. 5 is a cross-sectional view schematically showing a fourth embodiment of an apparatus for evaluating gas barrier properties of the present invention.

As shown in FIG. 5, an apparatus 10 (10d) for evaluating gas barrier properties according to the fourth embodiment has a structure similar to that of the apparatus 10b for evaluating gas barrier properties shown in FIG. 3, except that a permeation-side gas inlet pipe 71 and a permeation-side gas outlet pipe 72 are connected with a permeation-side chamber 41, and that a mass spectrometer (atmospheric pressure ionization mass spectrometer) that can analyze a normal-pressure gas through the permeation-side gas outlet pipe 72 is provided as a detection unit 33.

After the apparatus 10d for evaluating gas barrier properties is started up, dry nitrogen is progressively fed into a space on the permeation side from the permeation-side gas inlet pipe 71, with a permeation-side chamber 41 and a pipe 72 communicated are heated to 100° C., and this condition is held for one week (baking). The temperature is then lowered to room temperature and a favorable environment is maintained on the permeation side. Thus, in comparison with the case where no baking is applied, emission of oxygen or water vapor from the inner wall of the permeation-side chamber can be reduced, to enable measurement with high sensitivity.

When oxygen barrier properties are to be evaluated, dry nitrogen is introduced into a feed-side gas inlet pipe 73. Oxygen on the feed side flows into the permeation-side space 51 through the sample 1 and the support 2, and oxygen partial pressure discharged from the permeation-side gas outlet pipe 72 therefore rises. The rise is analyzed with high sensitivity by the detection unit 33 formed of the atmospheric pressure ionization mass spectrometer, and change thereof is examined. Thus, permeability with respect to oxygen can be evaluated in a manner similar to the procedures in the second embodiment.

In the present embodiment, it is unnecessary to open the permeation-side space to atmospheric air upon exchanging samples, so that the baseline of oxygen in the permeation-side space 51 can be kept low at all times. More specifically, the gas permeability can be immediately evaluated after the samples are exchanged. In the conventional method, the permeation-side space 51 inside the permeation-side chamber 41 is exposed to atmospheric air upon exchanging samples, and oxygen in atmospheric air is mixed thereinto. Therefore, it has been necessary to wait until the oxygen concentration becomes sufficiently low after samples are exchanged.

Furthermore, according to the present embodiment, the pressure on the feed side can be increased. Increasing the pressure on the feed side increases the driving force of oxygen permeation, so that a large amount of oxygen is permeated. As a result, a sample having low oxygen permeability can be readily evaluated.

In the apparatus 10 for evaluating gas barrier properties of the present invention, the gas permeability of the sample can be evaluated quickly, with high sensitivity, simply, and inexpensively, and high efficiency can therefore be achieved in the development of gas barrier films and the inspection of products prior to shipment. The thus developed and produced gas barrier film can be used for an organic electronics element, such as a solar cell or an organic light-emitting device, leading to an improvement in product life cycle. Moreover, the gas barrier film can be used, in place of a bottle or a can, for food packaging that allows transparent packaging enabling long-period storage and visual recognition of contents.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2013-017822 filed in Japan on Jan. 31, 2013, and Patent Application No. 2013-270502 filed in Japan on Dec. 26, 2013, each of which is entirely herein incorporated by reference.

REFERENCE SIGNS LIST

1 Sample
2 Support
31 Detection unit (pressure gauge)
32 Detection unit (mass spectrometer)
33 Detection unit (atmospheric pressure ionization mass spectrometer)
41 Permeation-side chamber
42 Feed-side chamber
51 Permeation-side space
52 Feed-side space
62 Valve
71 Permeation-side gas inlet pipe
72 Permeation-side gas outlet pipe
73 Feed-side gas inlet pipe
74 Feed-side gas outlet pipe

The invention claimed is:

1. An apparatus for evaluating gas barrier properties, comprising:
   a polymer-containing support for supporting a sample;
   a chamber disposed on a permeation side of the support; and
   a detection unit,
   wherein the support is connected with and closes an opening of the chamber disposed on the permeation side, and
   wherein glass transition point of the polymer contained in the support is 100° C. or higher.

2. The apparatus for evaluating gas barrier properties according to claim 1, wherein the support is made of an organic/inorganic composite.

3. The apparatus for evaluating gas barrier properties according to claim 1, wherein a pressure inside the chamber on the permeation side is lower than atmospheric pressure.

4. The apparatus for evaluating gas barrier properties according to claim 1, wherein the detection unit is a pressure gauge.

5. The apparatus for evaluating gas barrier properties according to claim 1, wherein the detection unit is a mass spectrometer.

6. A method for evaluating gas barrier properties, comprising:
   providing a polymer-containing support for supporting a sample, a chamber disposed on a permeation side of the support, and a detection unit,
   the support being connected with and closing an opening of the chamber disposed on the permeation side, and
   glass transition point of the polymer contained in the support being 100° C. or higher,
   wherein the chamber disposed on the permeation side is heated to 100° C. or higher before mounting the sample onto the support.

* * * * *